US008687857B2

(12) United States Patent  (10) Patent No.: US 8,687,857 B2
Bello et al.  (45) Date of Patent: Apr. 1, 2014

(54) SYSTEMS AND METHODS FOR AUTOMATED EXTRACTION OF HIGH-CONTENT INFORMATION FROM WHOLE ORGANISMS

(75) Inventors: Musodiq O. Bello, Niskayuna, NY (US); Jens Rittscher, Ballston Lake, NY (US); Ahmad Yekta, Somerset, NJ (US); Dirk Ryan Padfield, Albany, NY (US); Jilin Tu, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 683 days.

(21) Appl. No.: 12/267,019

(22) Filed: Nov. 7, 2008

(65) Prior Publication Data

US 2010/0119127 A1   May 13, 2010

(51) Int. Cl.
*G06K 9/00* (2006.01)

(52) U.S. Cl.
USPC .......................................... 382/128; 382/130

(58) Field of Classification Search
None
See application file for complete search history.

(56) References Cited

U.S. PATENT DOCUMENTS

| | | | |
|---|---|---|---|
| 6,656,449 | B1 | 12/2003 | Serbedzija et al. |
| 6,657,713 | B2 | 12/2003 | Hansen |
| 7,116,407 | B2 | 10/2006 | Hansen et al. |
| 7,176,016 | B2 | 2/2007 | Maher et al. |
| 7,390,648 | B1 | 6/2008 | Palacios-Boyce |
| 2002/0025297 | A1 | 2/2002 | Serbedzija et al. |
| 2004/0261143 | A1 | 12/2004 | Mumm et al. |
| 2006/0104905 | A1 | 5/2006 | Serbedzija et al. |
| 2007/0178012 | A1 | 8/2007 | Ferrante |
| 2008/0240527 | A1* | 10/2008 | Keller .......................... 382/128 |

FOREIGN PATENT DOCUMENTS

| | | |
|---|---|---|
| WO | WO2006135677 | 12/2006 |
| WO | WO2007014318 | 2/2007 |
| WO | WO2007054735 | 5/2007 |
| WO | WO2007110555 | 10/2007 |

OTHER PUBLICATIONS

Kabil et al., "Magnetic Resonance Microscopy of the Adult Zebrafish" Dec. 1, 2006, 3(4): 431-439.
Mason et al., "The Potential of Optical Coherence Tomography in the Engineering of Living Tissue", Phys. Med. Biol. 49 (2004) 1097-1115.
Kane et al., "Fish Models in Behavioral Toxicology: Automated Techniques, Updates and Perspectoves", (2005), pp. 1-38.
Ton et al., "Zebrafish as a Model for Developmental Neurotoxicity Testing", Birth Defects Research (Part A) Clinical and Molecular Teratology, 76:553-567 (2006).
Tran et al., "Automated, Quantitative Screening Assay for Antiangliogenic Compounds Using Transgenic Zebrafish", Cancer Research 2007; 67: (23)Dec. 1, 2007 11386-11392.
Razvi, "High Content Screening", Report 9213, Mar. 2006, 1-1 to 3-14, Appendix I and Appendix II.

(Continued)

*Primary Examiner* — Minh N Tang
(74) *Attorney, Agent, or Firm* — Jenifer Haeckl (57) ABSTRACT

Systems and methods for extracting information about an organism of interest, such as an atlas of the organism of interest; a storage device for at least temporarily storing an image of the organism of interest; and an operating device that automatically creates a map of the image of the organism of interest and automatically compares the map of the image to the atlas of the organism.

30 Claims, 8 Drawing Sheets

(56) References Cited

OTHER PUBLICATIONS

Parng et al., "A Zebrafish Assay for Identifying Neuroprotectants in Vivo", Neurotoxicology and Teratology, (2006), pp. 1-8.
Kimmel et al., "Stages of Embryonic Development of the Zebrafish", Developmental Dynamics 203:253-310 (1995).
Vogt, "High-content Analysis of Zebrafish Angiogenesis by Cognition Network Technology", Cambridge Healthtech Institute's Fifth Conf. on High-Content Analysis, SanFrancisco, CA, 2008, pp. 1-23.
Liu, A Quantitative Zebrafish Phenotyping Tool for Developmental Biology and Disease Modeling, IEEE Signal Processing Magazine, Jan. 2007, pp. 126-129.
Geisler et al., "Automated Multiparametric Platform for High-Content and High-Throughput Analytical Screening on Living Cells", IEEE Transactions on Automation Science and Engineering, vol. 3, No. 2, Apr. 2006, pp. 169-176.
Peng, "Bioimage Informatics: a New Area of Engineering Biology", Bioinformatics, vol. 24, No. 17, 2008, pp. 1827-1836.
Stern et al. "Cancer Genetics and Drug Discovery in the Zebrafish", Natrure Reviews, vol. 3, Jul. 2003, pp. 1-7.
Lamerton et al., "Cellular Imaging in Drug Discovery: Technical Advances in Fluorescence Microscopy for HTS", Life Science News 17, 2004 Amersham Biosciences, pp. 4-6.
Liu et al., "Computerized Image Analysis for Quantitative Neuronal Phenotyping in Zebrafish", Journal of Neuroscience Methods 153 (2006) pp. 190-202.
Lam et al., "Conservation of Gene Expression Signatures Between Zebrafish and Human Liver Tumors and Tumor Progression", Nature Biotechnology, vol. 24, No. 1, Jan. 2006, pp. 73-75.
Rinneret Al., "Contrast Sensitivity, Spatial and Temporal Tuning of the Larval Zebrafish Optokinetic Response", Investigative Opthalmology & Visual Science, Jan. 2005, vol. 46, No. 1, pp. 137-142.
Li et al., "Detection of Blob Objects in Microscopic Zebrafish Images Based on Gradient Vector Diffusion", Cytometry, Part A, 71A, 2007, pp. 835-845.
Peterson, "Discovery of Therapeutic Targets by Phenotype-based Zebrafish Screens", Elsevier Technologies, 2004, pp. 49-54.
Milan et al., "Drugs that Induce Repolarization Abnormalities Cause Bradycardia in Zebrafish", Circulation, 2003; 107: 1355-1358.
Canaple et al., "Fast Screen of Paramagnetic Molecules in Zebrafish Embryos by MRI". NMR in Biomedicine, 2008; 21: pp. 129-137.
Zhou, "High Content Cellular Imaging for Drug Development", IEEE Signal Processing Magazine, Mar. 2006, pp. 170 174.
Rausch, "High Content Cellular Screening", Current Opinion in Chemical Biology, 2006, 10: pp. 316-320.
Nature Reviews, "High-Content Screening-Integrating Information", vol. 7, Feb. 2008, 1 page.
Burns et al., "High-throughput Assay for Small Molecules that Modulate Zebrafish Embryonic Heart Rate", Nature Chemical Biology, vol. 1, No. 5, Oct. 2005, pp. 263-267.
Zon et al. "In Vivo Drug Discoveryin the Zebrafish", Nature Reviews, vol. 4, Jan. 2005, pp. 35-44.
Berghmans et al., "Making Waves in Cancer Research: New Models in the Zebrafish", BioTechnologies, vol. 39, No. 1 (2005) pp. 1-11.
Brockerhoff, "Measuring the Optokinet Response of Zebrafish Larvae", Nature Protocols, vol. 1, No. 5, 2006, pp. 2448-2451.
Wolf et al., "Qualitative and Quantitative Histomorphologic Assessment of Fathead Minnow Pimephales Promelas Gonads as an Endpoint for Evaluating Endocrine-Active Compounds: A Pilot Methodology Study", Toxicology Pathology 2004, 32; 600, pp. 600-612.
Eggert et al., "Small Molecules Screening by Imaging", Current Opinion in Chemical Biology 2006, 10, pp. 232-237.
Verbeek et al., "A Standard 3D Digital Atlas of Zebrafish Embryonic Development for Projection of Experimental Data", IS&T/SPIE Conference on Internet Imaging, San Jose, CA. Jan. 2000, pp. 242-252.
Love et al., "Technology for High-Throughput Screens: the Present and Future Using Zebrafish", Current Opionion in Biotechnology 2004, 15, pp. 564-571.
Spence et al., "The Behaviour and Ecology of the Zebrafish, Danio Rerio", Biological Reviews 83 (2008) pp. 13-34.
Spitsbergen et al., "The State of the Art of the Zebrafish Model for Toxicology and Toxicologic Pathology Research—Advantages and Current Limitations", Toxicologic Pathology, vol. 31 (Suppl), pp. 61-87, 2003.
Collins et al., "Transforming Environmental Health Protection", Science, vol. 319, Feb. 15, 2008, pp. 906-907.
Verbeek et al., "Visualization of Complex Data Sets Over Internet: 2D and 3D Visualization of the 3D Digital Atlas of Zebrafish Development", Proceedings of SPIE, vol. 4672 (2002), pp. 20-29.
Patricia McGath & Chun-Qi Li, "Zebrafish: A Predictive Model for Assessing Drug-Induced Toxicity", 2008, pp. 1-8.
Hill et al., "Zebrafish as a Model Vertebrate for Investigating Chemical Toxicity", Toxicological Sciences, 86(1), 2005, pp. 6-19.
Padfield et al., "Zebrafish FFT Registration: Translation, Rotation and Scale", Sep. 13, 2008, pp. 1-16.
Liu et al., "ZFIQ: A Software Package for Zebrafish Biology", Bioinformatics, vol. 24, No. 3, 2008, pp. 438-439.

* cited by examiner

SYSTEMS AND METHODS FOR AUTOMATED EXTRACTION OF HIGH-CONTENT INFORMATION FROM WHOLE ORGANISMS

BACKGROUND

The invention relates generally to automated systems and methods for extracting high-content information from whole organisms.

Organisms, such as teleosts, nematodes and fruit flies serve as biological models for a variety of research applications. For example, zebrafish is a well-known vertebrate model for developmental biology, molecular genetics, and toxicology studies. Zebrafish offer many advantages over other research models such as mice including the small size of zebrafish, low husbandry costs, ex utero transparent embryos, early morphology distinction, large number of embryos produced per mating, and the similarity of its genome to that of humans. Zebrafish are commonly used to study the effect of various drugs on cell apoptosis, organ development (e.g. brain, liver, tail, ear) as well as cardiac and nervous system functions.

Research using zebrafish as the model organism has extended to modeling human diseases and analyzing the formation and functions of cell populations in organs within the organism. This work has generated new human disease models and has begun to identify potential therapeutics, including genes that modify disease states and chemicals that rescue organs from disease.

The recent development of the zebrafish as a model for chemical genetics has established chemical screening in vivo as an adjunct to older screening technologies in cell lines or in vitro. Soluble chemicals permeate into zebrafish embryos and produce specific effects. In contrast to screening by in vitro techniques, zebrafish offers an in vivo vertebrate model for studying the bioactivity of chemicals. In addition, the availability of large numbers of zebrafish mutants makes chemical suppressor screens fast and straightforward. The targets of chemicals found to prevent or cure disease phenotypes in zebrafish will, in general, have very close cognates in humans. Therefore these screens promise to provide key entry points for the development of new therapeutic drugs.

In contrast to other vertebrate models, zebrafish complete embryogenesis in the first 72 hours post fertilization. Most of the internal organs, including the cardiovascular system, gut, liver and kidney, develop rapidly in the first 24 to 48 hour. Zebrafish embryos are also transparent, which facilitates observation and analysis. All the precursor tissues of the brain, eyes, heart and musculature can be easily visualized using light microscopy. Another important advantage of this animal model is that the morphological and molecular basis of tissue and organ development is, in general, either identical or similar to other vertebrates, including humans. Use of zebrafish as an alternative animal model for mammals accelerates research and is less expensive than large animal testing.

However, use of zebrafish for preclinical testing requires the researcher to take various anatomical measurements such as, but not limited to, liver size, tail length and curvature, size and frequency of spots, and the presence or absence of axons. At present, these measurements are typically obtained manually, or using generic imaging software and manual tracing of image features. Such methods are time consuming and inefficient given the small size of these research models and subject to human bias. One approach is to develop image analysis algorithms specific to the observable phenotypes of each assay. While the latter method can be functional, it is inefficient in that time and effort must be spent for each specific assay.

Although various methods exist that use atlases of various anatomical features to guide such generic segmentation and registration software, such methods are deficient or otherwise not capable of registering the atlases on an actual organism without substantial augmentation. Although methods exist that are capable of imaging small portions of a nematode research model at the cellular level, these methods are not capable of automatically imaging and mapping whole research models. These methods are also not adapted for use in automated screening.

Currently, automated, medium- or high-throughput systems and methods do not exist for quantitatively measuring and analyzing whole, but small, organisms, such as zebrafish, which are necessary to make them a viable alternative to larger research models such as mice.

BRIEF DESCRIPTION

The systems and methods of one or more of the embodiments facilitate research and screening efforts including, but not limited to, various studies in organisms and research models, such as zebrafish, by providing high-content, medium-throughput, automated systems and methods for measuring and analyzing research-relevant features and phenotypic information from the organisms. For example, one or more embodiments of the high-content systems use spatially or temporally resolved methods to obtain multiple informational vectors in parallel to facilitate integrated analysis. These systems and methods enable in vivo assessment of compounds and environmental chemicals and their side effects in whole animal models, or in multiple tissues or organs of animal models simultaneously or over time and across different doses. When used in high-content, automated systems, the systems and methods enable rapid, automated and extensive compound screening such as the screening of compound libraries.

One example embodiment of the system for extracting information about an organism of interest, generally comprises, an atlas of the organism of interest; a storage device for at least temporarily storing an image of the organism of interest; an operating device that automatically creates a map of the image of the organism of interest and automatically compares the map of the image to the atlas of the organism.

The atlas may comprise delineation of regions and/or sub-regions within the organism such as, but not limited to, organs within the organism, and portions of the organs. The digital atlas of one or more of the embodiments may be adaptable to a given organism of interest, either automatically or by adaptations initiated by the user.

The operating device may automatically determine a developmental stage of the organism, and may in part use an automated fitting algorithm to compare the map of the image to the atlas of the organism. The atlas may be annotatable via the operating device.

In one or more of the embodiments of the methods and systems, the operating device generates one or more measurements of the organism of interest, wherein one or more of the measurements comprise measurements of one or more anatomical features and/or developmental defects of the organism of interest. In at least one of the example embodiments, the measurements have a variance of less than five percent. In one or more of the embodiments, the measurements comprise one or more of length, area and curvature. In one or more of the embodiments, the atlas may register to the image of the organism acquired with transmitted light imaging modality (e.g., brightfield), identify the regions of interest, and further register to the image of the same field of view acquired by fluorescence imaging modality. In this example embodiment, the measurements comprise one or more determinations based on morphometric (e.g. length, area and curvature) or intensity based (e.g. signal level, signal granularity) measures.

The operating device may automatically determine a development stage of the organism of interest and/or a development stage of a characteristic or feature of the organism of interest.

The operating device, in one or more of the embodiments, may use an atlas to correct one or more imaging characteristics of the image of the organism of interest. An example of the system further comprises an imaging device wherein the imaging device takes a plurality of images of the organism of interest and may be configured to take images at various levels of resolution. For example, one of the images is a lower resolution image of the entire organism and one of the images is a higher resolution image of one or more organs within the organism of interest. One or more of the embodiments comprise an imaging device that takes images at various levels of resolution automatically, based at least in part, on the comparison of the image of the organism of interest to the atlas of the organism of interest. One example embodiment also comprises an imaging device that is configured to automatically employ the atlas at lower resolution to determine the areas of interest and focus and image at higher resolution on the regions of the organism's body.

The storage device, in one or more of the embodiments, may also store information on one or more agents. In such embodiments the operating device may also gather data relating to one or more organs within the organism of interest and correlate the data with the information on one or more agents. Measures may be obtained from several imaging modalities, including but not limited to, transmitted light imaging in different color channels (wavelength bands) and fluorescence imaging in one or more wavelength channels.

An example embodiment of the operating device may also determine the presence of one or more toxins in the organism of interest and may further determine one or more levels of toxicity based on the correlation of the organ data to the probe information.

An example method for extracting information about an organism of interest, generally comprises, providing an atlas of the organism of interest; providing an image of the organism of interest; automatically creating a map of the image of the organism of interest; and automatically comparing the map of the image to the atlas of the organism. In one example embodiment, at least one of the images is acquired in the transmitted light modality. One or more of the embodiments of the methods measure one or more features of the organism of interest, wherein one or more of the measurements comprise measurements of one or more anatomical features of the organism of interest, and wherein the measurements may comprise length, area and curvature. The variance between similar measurements, in one or more of the embodiments, may be configured to be less than five percent, depending on the desired level of accuracy for a given system.

One or more of the embodiments of the methods determine whether the organism is of a predetermined strain of organism and may be configured to determine a development stage of the organism of interest. One or more of the embodiments of the methods allow the user to use images of several (e.g. more than 10) samples of healthy untreated organisms to operate the storage device and train the existing atlas to define and generate a new atlas. In this example, small variations of the organism set, used to define the original atlas from the users atlas, will not result in erroneous measures on the samples. Such variation may arise because the original organisms may have been from differing strain (e.g. genetic variation) and/or from differing stages (e.g. developmental variation).

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The systems and methods of one or more of the embodiments enable medium-throughput, automated measurements of various morphological features and other relevant biological and chemical information about a given organism of interest. One or more of the embodiments may also be configured to generate scores based on a combination of measurements and/or other information relevant to research. For example, for a given assay, a set of morphological and textural descriptors may be extracted from each fish being screened, as well as for specific organs and subparts of organs within the fish. In one or more of the embodiments of the systems and methods, an atlas of the model organism is used as the standard or model to which the organism, being screened, is compared. Such shape and appearance descriptors are stored, in some of the embodiments of the systems, as metadata, or are otherwise accessible to the system's operating subsystem. In one or more example embodiments, a query regarding a particular fish will result in various scores for individual toxicology endpoints. In one or more example embodiments, a query regarding a particular toxicology endpoint will produce the fishes that have high scores for specific features relating to that endpoint.

One or more of the embodiments of the system for extracting information about an organism of interest, generally comprises an atlas of the organism of interest; a storage device for at least temporarily storing an image of the organism of interest; and an operating device that automatically creates a map of the image of the organism of interest and automatically compares the map of the image to the atlas of the organism.

To more clearly and concisely describe and point out the subject matter of the claimed invention, the following definitions are provided for specific terms, which are used in the following description and the appended claims. Throughout the specification, exemplification of specific terms should be considered as non-limiting examples.

As used herein, the term "atlas" refers to a graphical representation of an organism's anatomy ontology. The atlas may be a graphical representation of the entire organism or may be divisible into portions or regions of the organism. The representation may be from a single organism or may be synthesized and averaged from a group of individual organisms. The atlas may comprise one or more of a representation of an organism on which the spatial extent and coordinates of the representation is defined; an ontology of terms; and a mapping, or interpretation, between the representation and the ontology. The ontology may comprise the structural changes that occur during development of the organism (e.g. embryonic development stages) and may further comprise one or more hierarchies, for each development stage, wherein a stage may be characterized by internal and external morphological features of the organism.

As used herein, the term "organism" refers to a whole being that when living, is capable of serving as a research model for a human being, comprising one or more organs within the organism that, at least for research purposes, mimics or is comparable to one or more of a human's organs. Examples of such organisms include, but are not limited to, teleosts, nematodes, and arthropods. As used herein, the term "organ" refers to a group of tissues that perform a specific function or group of functions (e.g. heart, lungs, brain, eye, stomach, spleen, bones, pancreas, kidneys, liver, intestines, skin, urinary bladder and sex organs).

As used herein, the phrase "map of the image of the organism of interest" refers the identification of one or more key features of the organism necessary to registering an atlas on one or more images of the organism, wherein such features include, but are not limited to, organs within the organism.

As used herein, the term "annotation" refers to words, symbols, letters, images, numbers, marks and phrases that may be added, deleted, amended, or replaced. Annotations may be entered by the system based on preset guidelines or rules or by system-adaptable guidelines or rules, or by a user of the system. The annotations may be entered manually, automatically, or electronically using a keyboard, a stylus, touchpad, or using verbal identification software. The means of entry may be hardwired or wireless. Annotations may be, but are not limited to, semantic, textual, explanatory, commentary, illustrative, automated, pictorial, auditory, or linguistic in nature. Annotations may be visible to the viewer on-screen, embedded, hypertext, archived or retrievable, without limitation.

As used herein, the term "agent" refers to any element, compound, or entity including, but not limited to, e.g. pharmaceutical, therapeutic, pharmacologic, environmental or agricultural pollutant or compound, toxin, aquatic pollutant, cosmeceutical, drug, toxin, natural product, synthetic compound, or chemical compound.

As used herein, the term "developmental defect" refers to deficiency, imperfection, or difference in the development of a tissue, organ, or other bodily component of an organism relative to normal development. Such a defect may be identified as a change, difference, or lack of something necessary or desirable for completion or proper operation in the development of a tissue, organ, or other bodily component of an organism.

As used herein, the term "toxin" refers to any substance that has the potential to cause harm to the organism.

Although the examples described are directed at zebrafish (a species of teleost), these methods and systems can be adapted for use with other whole model organisms, at any suitable developmental stage, such as, but not limited to, other suitable species of teleosts (e.g. medaka, Giant rerio, and puffer fish), nematodes and fruit flies.

The example methods and systems automate the analysis of zebrafish for various research and screening studies such as toxicology studies. Measurements of the fish, such as, but not limited to, the length of the fish, number of spots on the head and tail, curvature of the tail, and liver shrinkage are carried out automatically use various shape descriptors based on models of the fish. Images may be acquired by various modalities as in transmitted light and fluorescence imaging, each in various spectral bands, or in combination constituting hyperspectral imaging. The shape descriptors may be stored in a database in a memory device as hardware in the system or otherwise accessible to the system via a removable memory device or through a server. These shape descriptors facilitate the search and comparison of fish phenotypes to the organism of interest being screened. Furthermore, such databases can be integrated with other zebrafish databases (e.g., gene databases on ZFIN). The extraction of shape and appearance features at the organ level mimics the current approach of toxicologists. However, the database may also serve as a discovery tool in which several features can be combined to qualify a phenotype.

One aspect of the methods and systems is to enable detection and identification of the development stage of an organism. Depending on the organism of interest, the developmental stage of a given organism is important when detecting and identifying the anatomy of the organism. At least one of the example embodiments of the methods and systems detects the developmental stage of an organism automatically. Another aspect of the methods and systems is to enable detection and identification of the viability of the small organism for the initial screening before the start of compound treatment studies (dead vs. alive).

Another feature of some of the embodiments of the methods and systems is automated image analysis. Automated image analysis enables process standardization that is very important for screening the effects of drugs and toxins on organisms and organ development. For example, automated image analysis of zebrafish enables repetitive tasks, detect rare events, quantify the extent of different stains, classify and count numerous features, and answer questions that are beyond the capabilities of manual microscopy. In the context of modeling, it is essential to have quantified data of the biological and image-based experiments. High-throughput image analysis is the most practical way to accomplish such a task.

Another feature of one or more of the embodiments is to detect and identify the anatomical structures of the organism. The term atlas is used herein refers to the description of a model organism's anatomy. At least one embodiment of the methods and systems may be configured to detect and identify the various developmental stages of the organism. Although the atlas may be constructed in various ways, at least one embodiment of the atlas is constructed using a 2-dimensional deformable mesh. A given set of measurements may be defined using the vertices of the mesh.

Figure 1:
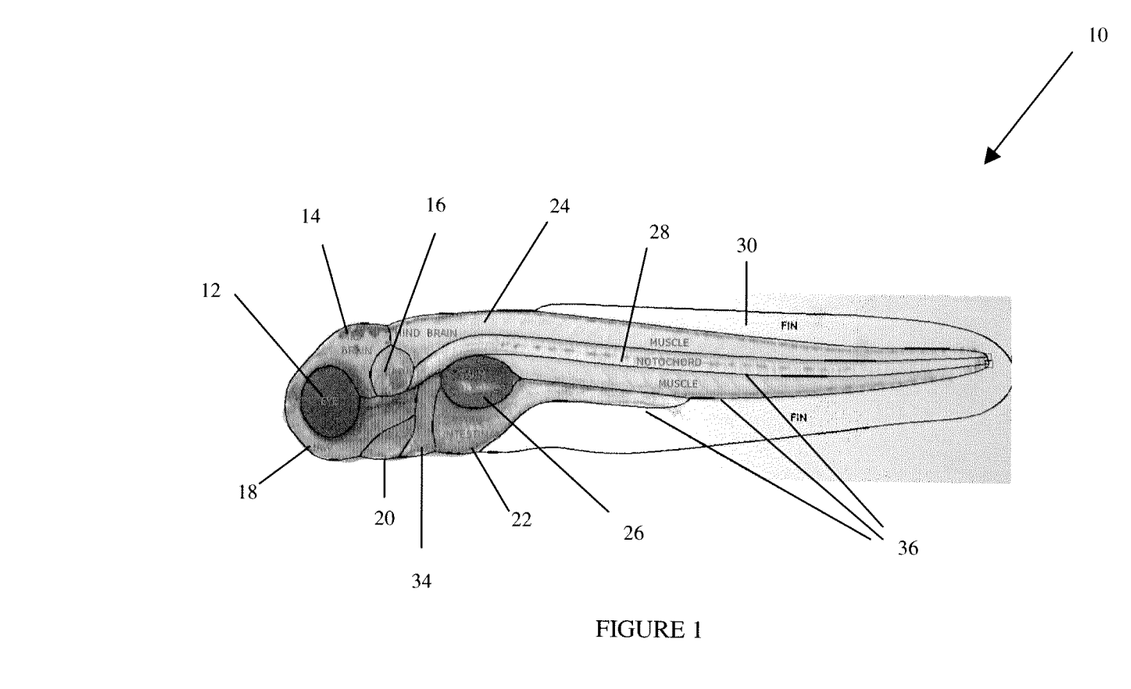
FIG. 1 is a diagram of an embodiment of an atlas useful in one or more of the systems and methods of the invention.

The atlas for a given organism should capture all the relevant regions of the organism. A non-limiting example of such an atlas is shown in FIG. 1 for a zebrafish that is approximately 5-days-old (120 hours). The atlas 10 comprises twelve anatomical regions. In this example, the regions shown are the eye 12, mid brain 14, ear 16, jaw 18, liver 20, intestine 22, hindbrain 24, bladder 26, notochord 28, muscle 30, fin 32, and heart 34. In this example, subdivision surfaces 36 are incorporated to model the shape and regions of the individual fish at multiple resolutions. The methods may also be used to construct an atlas in three dimensions (3D). Both the atlas generation and the automatic atlas registration do not depend on the dimensionality of the data. For example, an atlas may be three dimensional (3D) whereby the image of the fish is acquired as a set of Z-stack images taken orthogonal to the sagittal or axial direction, or two images in stereo or two images in two different axes. An atlas may also incorporate a time component (2D+time or 3D+time) in which the image is taken repeatedly over time (e.g. to measure cardiac rate.

Figure 2:
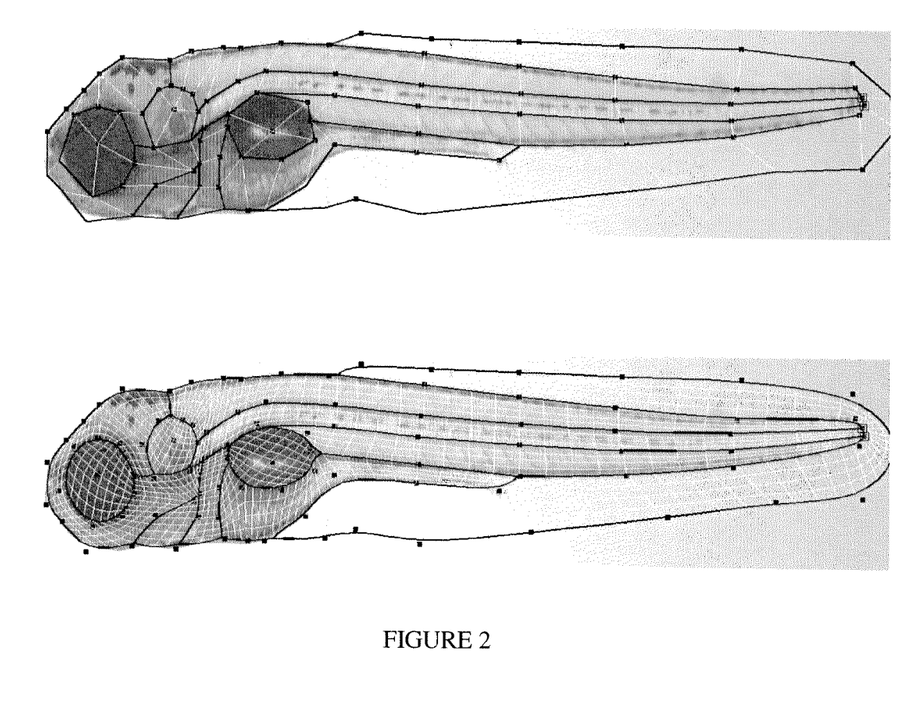
FIG. 2 is a diagram of an embodiment of subdivision levels of the atlas shown in FIG. 1.

FIG. 2 is an example of an atlas showing two levels of subdivision surfaces. The first level subdivides each region into large sub-regions 38 and the second level subdivides each region into smaller sub-regions 40. The variety in size, shape and purpose of the subdivisions may be adapted for a given application. Although these example atlases comprise all the major anatomical features of a zebrafish, these examples are not limiting. The atlas may be refined and adapted by the user as needed for a given organism. For example, a user may annotate a certain sub-region of the atlas as a region of interest.

Atlases may also be created for a variety of uses such as phenotyping studies. For example, atlases may be created for a sub-population such as a mutant strain or for subpopulations used in knock-out studies.

In one or more of the embodiments of the methods and systems, an automatic fitting algorithm is used to register or otherwise match or compare the atlas to the example of the individual fish. Once registered, the system may be configured to carry out a variety of measurements and analyze the sample fish being tested. The type of measurements and analysis can be automatically generated by the system based on, for example, the type of organism, assay or test. The user may also make selections or enter customized instructions into the system as needed.

Figure 5:
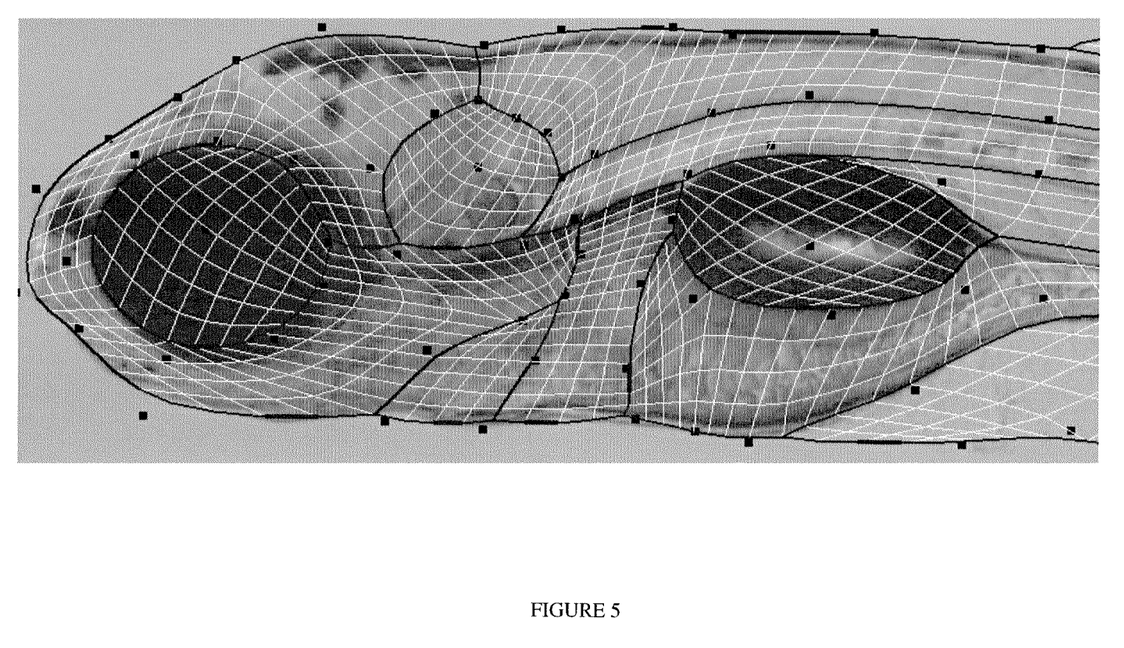
FIG. 5 is an embodiment of a magnification of a sub-region of an organism of interest.

As shown in FIG. 5, the regions and sub-regions of the organism being tested may be automatically or selectively, enlarged, enhance or otherwise analyzed, by the system or user. For example, if an assay or toxicity test is directed at the effect on the liver, the system could automatically identify the liver region and then automatically enlarge or otherwise digitally or optically enhance and/or analyze the liver region. If a sub-region is subsequently identified as a sub-region of interest within the liver region, then the system could further enlarge, enhance and/or analyze the sub-region of interest. The map of the organism that is the subject of a given assay or test could be automatically or manually annotated by the system or user to mark, for example, a sub-region showing an anomaly.

As another example, if a given assay requires the measurement of the uptake of a fluorescent marker in a region of the zebrafish notochord, a user could mark the region as a region of interest in the atlas. The system could then measure and/or analyze the region of interest and generate a report or analysis of one or more features or characteristics of the region or sub-region.

Figure 3:
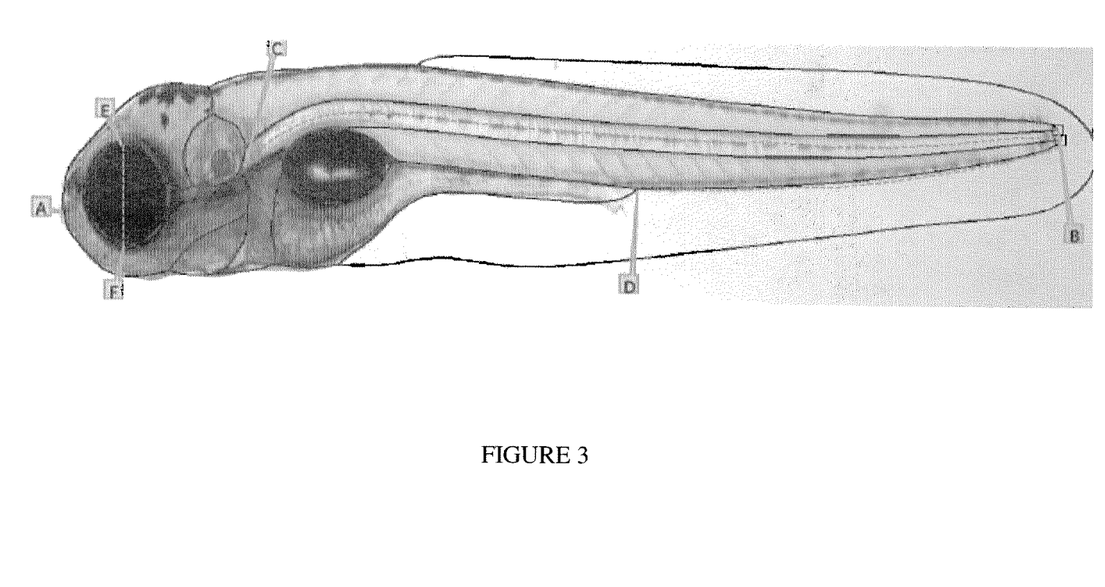
FIG. 3 is an illustration of an embodiment of a set of length and area measurements of a zebrafish.

A feature of one or more of the embodiments, when using an atlas, is the ability of the system to automatically carry out anatomically relevant measurements as defined by the structure of the atlas. Once the atlas is registered to a particular fish sample, any or all of the measurements can be computed automatically. An example of a possible set of area and length measurements is shown in FIG. 3 for a 5 day old zebrafish. In this example, the length measurements are based at least in part on the dotted lines on the fitted map. The area measurements are based at least in part on the solid lines on the fitted amp. For illustration only, area and length measurements, as shown in FIG. 3, for a zebrafish may comprise the following:

| Length Measurements | |
| --- | --- |
| AB | body length |
| BC | notochord length |
| BD | tail length |
| EF | eye size |
| Area Measurements | |
| Eye | |
| Swim bladder | |
| Heart chamber | |
| Gastro-intestinal tract | |
| Liver | |

Figure 4:
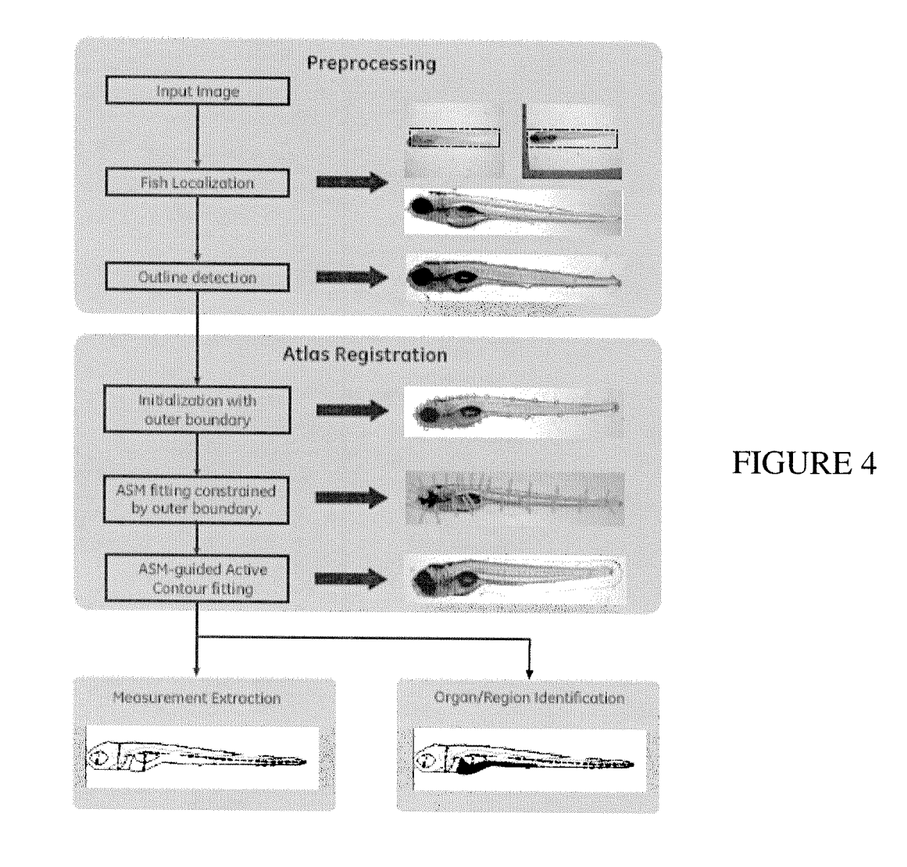
FIG. 4 is a flow diagram of an embodiment of an atlas-based measurement process useful in one or more of the systems and methods of the invention.

A general flow diagram is shown in FIG. 4 of an example of an atlas based measurement process. The process in this example begins with a digitized image of a zebrafish, preferably acquired with transmitted light imaging modality. During a preprocessing step, the foreground regions that belong to the fish are extracted, and key features, such as the head, eye and tail are detected and mapped. Key features may be detected using an algorithm comprising, for example to detect a zebrafish eye, a multi-resolution Hough circle fitting algorithm with a binary search for optimal radius. Zebrafish whole-body segmentation may be achieved, but is not limited to, using an algorithm comprising quadtree decomposition of the image based on region variance and merging similar blocks.

After the preprocessing step and before the measurements are extracted, the atlas, an example of which is shown in FIG. 1, is then registered, or otherwise compared, to the mapped features of the sample organism and the segmentation boundaries are refined. Once registered, the system then measures and/or analyzes one or more of the regions, sub-regions, anatomical structures, features or characteristics of the sample in accordance with automatically predetermined, contemporaneously selected, or manually entered guidelines or instructions.

Automated atlas registration is used to fit the shape and key body regions of an organism, such as the zebrafish, to its digital atlas so that certain anatomical measurements can be automatically estimated or determined. The preprocessing step identifies one or more regions of interest in the organism. A global registration is applied to estimate the overall orientation and position of the organism in the image. Given the resulting region of interest, comprising one sample organism, the outline of the organism is identified using image segmentation. In one of the embodiments, a quad-tree method for image segmentation is applied to identify the outline of the sample.

An active shape model (ASM) algorithm may be employed to register the atlas to a sample. ASM comprises a shape model and an appearance model. Shape is represented using a set of pre-specified landmarks. ASM captures shape variations by training a principal component analysis (PCA) model from observed data. At each landmark, a local texture model is obtained by training a Gaussian model using the observed profile texture along the normal direction of the shape contour. Since organism shape can vary substantially from the norm, a localization procedure may be used to register the organism so that the ASM algorithm can be initialized at a solution very close to its global optima.

As shown in FIG. 4, ASM landmarks along fish contour are identified by optimizing the likelihood of the landmark segment length, curvature and image texture observations. The contour points may be considered as states and the sequential landmark assignment along the contour may be considered as a trajectory to be optimized. The global optimal assignment of the ASM landmarks may be obtained using a dynamic programming algorithm. After assignment of the outer ASM landmarks, the interior ASM landmarks are initialized by maximal likelihood estimation. In this example, since the statistics of fish contour shape is correlated with the statistics of the fish interior shape structure, the maximal likelihood initialization of the fish interior shape are close to the ground truth. The ASM fitting algorithm is then used to maximize the likelihood of the texture observation of the fish interior fixing the ASM contour landmarks on the detected fish contour. Further refinement of the ASM fitting is achieved by Active Contours so that the shape and geometry can be fitted with higher accuracy. Finally the ASM registration result is converted to atlas structure, and the automatic fish measurements can be carried out.

Measurements of a sample organism may be compared to a predetermined range of measurements to determine, for example, whether a given measurement falls outside of the normal range of measurements. High-throughput screening measurements may also, for example, be compared against all of the organisms screened in a given run. Parameters such as, but not limited to, mean and variance, may be used to differentiate between normal, wild-type, abnormal, and treated and untreated organisms, as well as toxicity and levels of toxicity. Measurements are not limited to geometrical measurements and may include, but are not limited to, variations in image intensity and color.

Example

Figure 6:
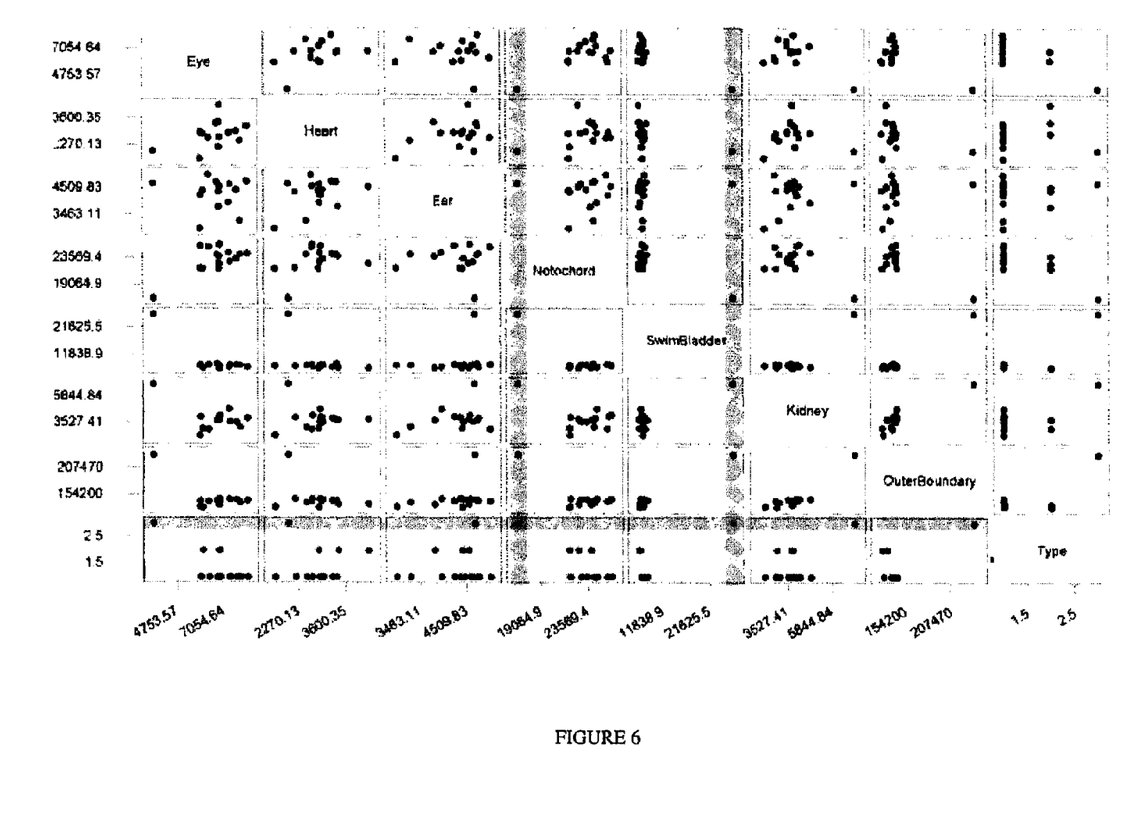
FIG. 6 is a matrix plot of an example of area measurements of a set of sample zebrafish.

A dataset of measurements were generated from eleven normal zebrafish, eight wild type zebrafish and one treated zebrafish. An atlas was then fitted to the set of fish and measurements were taken of the area of various organs within each of the zebrafish. FIG. 6 is a matrix plot of the area measurements.

The methods and systems may be configured to identify the developmental stage of an organism and to identify specific organs and sub-regions within the organs. Once identified, information about the organs and sub-regions may be further used to correlate the information according to an assay and/or an image of one or more fluorescent-based channels. An atlas of the organism is used in one or more of the embodiments to automatically locate the different organs in a zebrafish, for example, and then correlate the information to a predetermined set of rules or guidelines.

Figure 8:
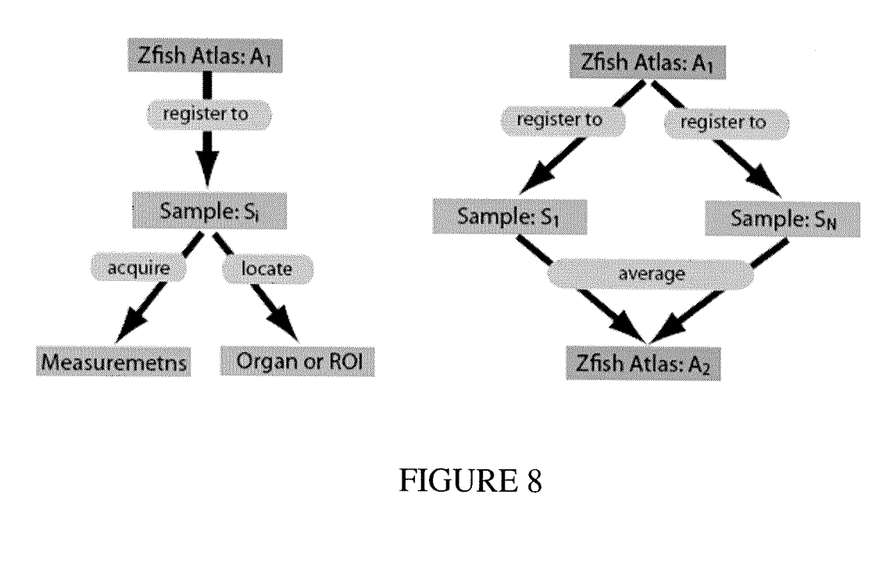
FIG. 8 comprises flow diagrams of embodiments of methods and systems for A) determining anatomically relevant measurements, B) identifying organs, and C) training an atlas for specific populations.

FIG. 8 illustrates non-limiting uses of the methods and systems. For example, the methods and systems may be used to determine anatomically relevant measurements, identify organs within the organism, and train an atlas for specific subpopulations. Measurements may include but are not limited to variations in length, area, curvature, color, grey-scale, intensity, texture, shape, fluorescence, and combinations thereof.

The methods and systems may also be used to analyze images of organisms taken in a plurality of varying planes (e.g. perpendicular) for 3D analysis. For example, the methods and systems may be adapted to image and analyze organisms having differentiated developmental stages that are suited to microwell assays and microfluidic devices such as, but not limited to, fertilized eggs and larvae, (e.g. *Danio rerio, Drosophila melanogaster, Xenopus laevis*) and fish such as fugu (puffer), medaka, Giant rerio, Paedocypris.

One or more of the embodiments of the methods and systems may comprise the steps and hardware for automatically acquiring one or more images of the sample organism. These automated imaging acquisition steps and the hardware needed for imaging the organism may be incorporated into automated, high-throughput screening systems such as an IN Cell system available from GE Healthcare.

In a first step, a low-resolution image is taken of the sample organism to locate the position of the organism and to detect the specific location of one or more organs of interest within the organism. This information is then applied to automatically change the objective of the system and position a movable stage to take a high-resolution image of the organ of interest. An atlas is also used in one or more of the embodiments to correct or otherwise automatically enhance an image, for example, by image stitching.

The system may comprise an imaging device that is configured to automatically employ the atlas at lower resolution to determine the areas of interest and focus and image at higher resolution on the regions of the organism's body. In this way the imaging throughput may be significantly increased. As an example of application, if the organism such as the zebrafish is in the wells of a 96-well plate, one 5-day post fertilization fish per well, and one is interested to imaging the heart region (size about 200 micrometer (um)), a suitable resolution may be to image with a 10× objective magnification. Under this magnification, the area of the typical field of view of an automated high content imaging system, e.g. the IN Cell 1000 from GE Healthcare, is about 0.6 mm². The circular well of a 96-well plate has a diameter of about 6.5 mm, or area of 33 mm². This implies that with the 10× objective at least 50 images must be acquired in each well until the heart area is imaged.

The operating device can be used to increase the speed of the system using, for example, the following steps: (1) acquisition of a single image of the whole well under 1× magnification; (2) online use of atlas analysis to locate the near exact value of the location of the heart area; (3) automated command of the motorized XY-stage movement to laterally move and center the heart area above the optical axis; (4) automated command of the motorized objective changer to change to a 10× objective; (5) automated command of the motorized Z-stage to axially move the objective to an appropriate level above the well bottom (e.g., 300 um, for better focusing); and/or (6) acquisition of transmitted and/or fluorescent images of the heart area. In some embodiments, all of the operations can be carried out simultaneously or nearly simultaneously, depending in part on whether multiple images are acquired. This example embodiment provides advantages such as, but not limited to, (a) high resolution imaging throughput can be increased significantly (at least 25 times in this example); (b) post processing of a large number of high resolution images is not necessary (e.g., analysis, stitching, flat field correction); and (c) system memory does not need to be hampered by the acquisition of a large number of useless images where most of the fields are empty.

The automated system 50 (FIG. 7) generally comprises: a memory storage device 52 for at least temporarily storing the atlas of the organisms and storing images of the sample organisms; and an operating device 54, such as a processor, for carrying out one or more of the steps of the methods. The memory storage device may comprise any suitable hard drive memory associated with the processor such as the ROM (read only memory), RAM (random access memory) or DRAM (dynamic random access memory) of a CPU (central processing unit), or any suitable disk drive memory device such as a DVD or CD, or a zip drive or memory card or stick. The memory storage device may be remotely located from the processor or the display device for displaying the images, and yet still be accessed through any suitable connection device or communications network including but not limited to local area networks, cable networks, satellite networks, and the Internet, regardless whether hard wired or wireless. The processor or CPU may comprise a microprocessor, microcontroller and a digital signal processor (DSP).

Figure 7:
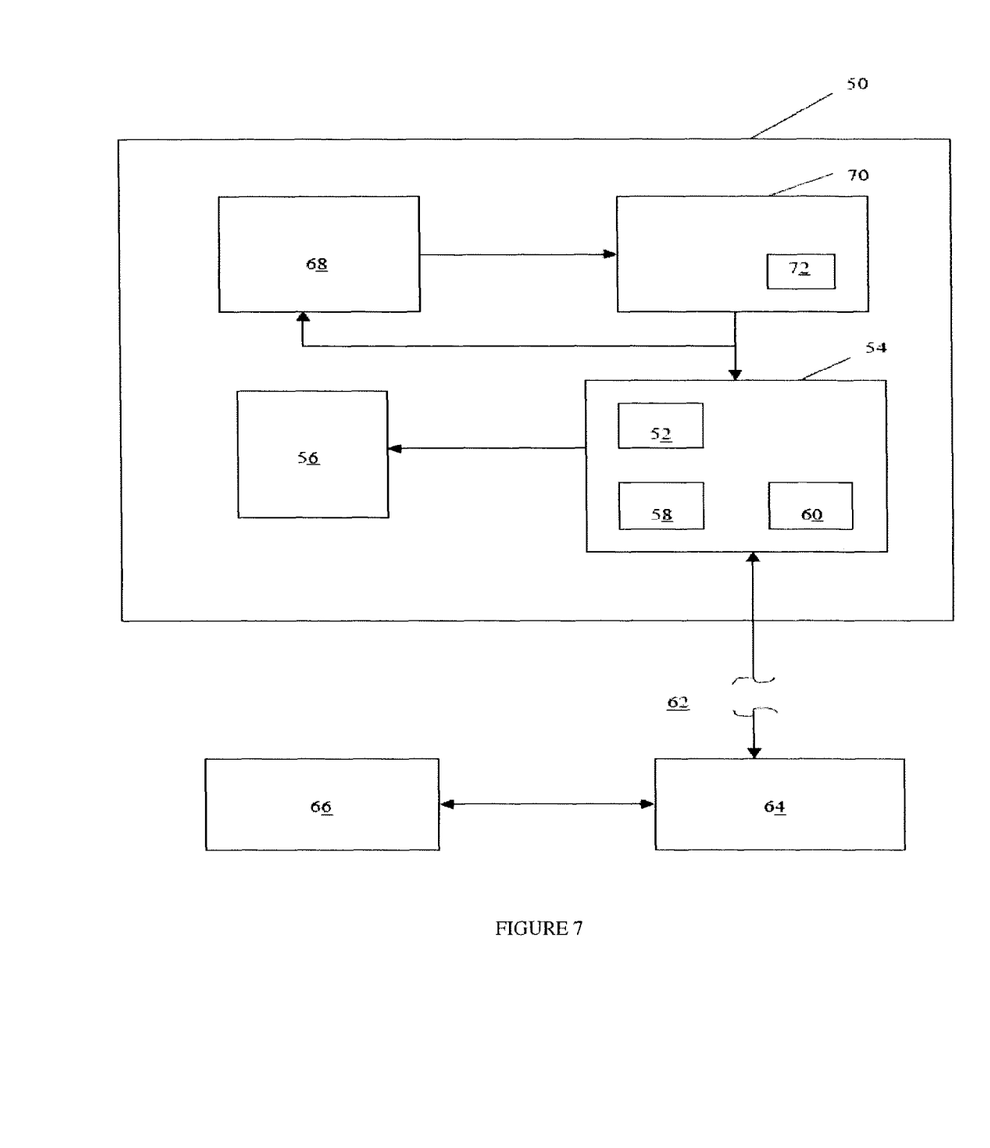
FIG. 7 is a diagram of an embodiment of an automated system of the invention.

The storage device 52 and the operating device 54 may be incorporated as components of an analytical device such as an automated high-speed system that images and analyzes in one system. Examples of such systems include, but are not limited to, the General Electric IN Cell Analyzer systems (General Electric Healthcare Bio-Sciences Group, Piscataway, N.J.). As noted, system 50 may further comprise a display device 56 for displaying one or more of the images of the sample organisms, the atlas, the atlas fitted on an image of the sample organism, measurement results and/or any other type of image, report or data useful for viewing by the user of the system; an interactive viewer 58; a virtual microscope 60; and/or a device for transmitting 62 one or more of the images or any related data or analytical information over a communications network 64 to one or more remote locations 66.

Display device 56 may comprise any suitable device capable of displaying a digital image such as, but not limited to, devices that incorporate an LCD or CRT. Transmitting device 62 may comprise any suitable means for transmitting digital information over a communications network including but not limited to hardwired or wireless digital communications systems. As in the IN Cell Analyzer, the system may further comprise an automated device 68 for processing assays or otherwise applying stains, markers, probes or other similar research tools; and a digital imaging device 70 such as, but not limited to, a fluorescent imaging microscope comprising an excitation source 72 and capable of capturing digital images of the sample organisms of interest. Such imaging devices may have a movable stage and may be capable of auto focusing and then maintaining and tracking the focus feature as needed.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for extracting information about a sample organism, wherein the sample organism is a small vertebrate that completes embryogenesis within approximately 72 hours following fertilization, the system comprising,
   an atlas registered to an organism of interest;
   a storage device for at least temporarily storing an image of the sample organism;
   an operating device that automatically creates a map of the image of the sample organism and automatically compares the map of the image to the atlas of the organism of interest; and
   an imaging device, wherein the imaging device takes one or more images of the sample organism, that is used to create the map, at a plurality of levels of resolution using a transmitted light imaging modality;
   wherein said transmitted light imaging modality is a high-throughput system.

2. The system of claim 1, wherein the atlas comprises delineation of organs within the organism.

3. The system of claim 1, wherein the small organism is at least partially transparent or translucent and visualized during embryonic development, and wherein the operating device automatically determines a developmental stage of the sample organism.

4. The system of claim 1, wherein the operating device in part uses an automated fitting algorithm to compare the map of the image of the sample organism to the atlas.

5. The system of claim 1, wherein the atlas is annotatable via the operating device.

6. The system of claim 1, wherein the operating device generates one or more measurements of the sample organism.

7. The system of claim 6, wherein one or more of the measurements comprise measurements of one or more anatomical features or developmental defects of the sample organism.

8. The system of claim 6, wherein the measurements have a variance, between sample organisms of the same type, of less than or equal to five percent.

9. The system of claim 6, wherein the measurements comprise one or more of length, area, curvature, color, texture, shape, and combinations thereof.

10. The system of claim 6, wherein the sample organism comprises precursor tissues that are visualized using the transmitted light imaging modality, wherein the transmitted light imaging modality is light microscopy.

11. The system of claim 1, wherein the operating device automatically determines whether the sample organism is of a predetermined strain of organism.

12. The system of claim 1, wherein the operating device determines a development stage of a characteristic or feature of the sample organism.

13. The system of claim 1, wherein the operating device detects one or more organs within the sample organism.

14. The system of claim 1, wherein the operating device uses the atlas to correct one or more imaging characteristics of the image of the sample organism.

15. The system of claim 1, wherein one of the images is a lower resolution image of the sample organism in its entirety and one of the images is a higher resolution image of one or more organs within the sample organism.

16. The system of claim 1, wherein the imaging device takes a plurality of images at various levels of resolution automatically, based at least in part, on the comparison of the image of the sample organism to the atlas.

17. The system of claim 1, wherein the storage device further stores information on one or more agents, and wherein the operating device gathers data relating to one or more organs within the sample organism and correlates the data with the information on one or more agents.

18. The system of claim 17, wherein the operating device determines one or more levels of toxicity based on the correlation of the organ data to probe information.

19. The system of claim 17, wherein the operating device determines the presence of one or more toxins in the sample organism.

20. The system of claim 1, wherein the sample organism is a zebrafish.

21. A method for extracting information about a sample organism during embryonic development, wherein the sample organism is a small vertebrate that is at least partially transparent or translucent and completes embryogenesis within approximately 72 hours following fertilisation, the method comprising,
   providing an atlas registered to an organism of interest;
   providing a plurality of images of the sample organism that are used to automatically create a map of the sample organism, wherein the images are taken at a plurality of levels of resolution with an imaging device using a transmitted light imaging modality; and
   automatically comparing the map of the image to the atlas.

22. The method of claim 21, further comprising, measuring one or more features of the sample organism.

23. The method of claim 22, wherein one or more of the measurements comprise measurements of one or more anatomical features of the sample organism.

24. The method of claim 22, wherein one or more of the measurements have a variance of less than or equal to five percent.

25. The system of claim 22, wherein the measurements comprise one or more of length, area and curvature.

26. The method of claim 22, further comprising, determining whether the sample organism is of a predetermined strain of organism.

27. The method of claim 22, further comprising, determining a development stage of the sample organism.

28. The method of claim 22, further comprising, determining one or more levels of toxicity in one or more organs in the sample organism.

29. The method of claim 22, further comprising, determining the presence of one or more toxins in the sample organism.

30. The method of claim 22, wherein the sample organism is a zebrafish embryo.

* * * * *